United States Patent [19]

Sele et al.

[11] 4,213,980
[45] Jul. 22, 1980

[54] AZATHIANAPHTHALENES

[75] Inventors: Alex Sele, Muttenz; Pier G. Ferrini; Georges Haas, both of Binningen; Knut A. Jaeggi, Basel; Alberto Rossi, Oberwil, all of Switzerland

[73] Assignee: Ciba-Geigy Corporation, Ardsley, N.Y.

[21] Appl. No.: 4,113

[22] Filed: Jan. 17, 1979

[30] Foreign Application Priority Data

Jan. 30, 1978 [CH] Switzerland ............................ 993/78

[51] Int. Cl.² .................... C07D 279/02; A61K 31/54
[52] U.S. Cl. ........................................ 424/246; 544/49
[58] Field of Search ........................... 424/246; 544/49

[56] References Cited

U.S. PATENT DOCUMENTS

| | | | |
|---|---|---|---|
| 3,591,584 | 7/1971 | Lombardino | 260/243 |
| 3,646,021 | 2/1972 | Zinnes | 260/243 |
| 3,892,740 | 7/1975 | Lombardino | 544/49 |
| 4,116,964 | 9/1978 | Zinnes et al. | 544/49 |

Primary Examiner—John M. Ford
Attorney, Agent, or Firm—John J. Maitner

[57] ABSTRACT 3,4-Dihydro-2H-1,2-benzothiazine 1,1-dioxides of the formula

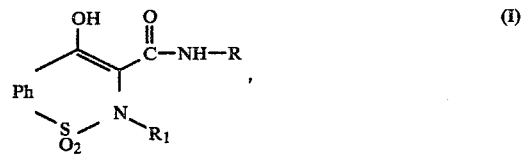

wherein Ph represents a substituted or unsubstituted 1,2-phenylene radical, R represents a substituted or unsubstituted benzopyrone radical, and $R_1$ represents hydrogen or a substituted or unsubstituted hydrocarbon radical of aliphatic character, and their salts, possess antiinflammatory properties and are useful as medicaments.

10 Claims, No Drawings

AZATHIANAPHTHALENES

The invention relates to novel azathianaphthalene derivatives, in particular to substituted 3,4-dihydro-2H-1,2-benzothiazine 1,1-dioxides of the formula I

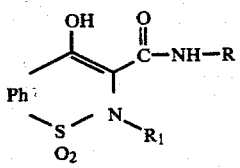

wherein Ph is a substituted or unsubstituted 1,2-phenylene radical, R represents a substituted or unsubstituted benzopyrone radical, and $R_1$ represents hydrogen or a substituted or unsubstituted hydrocarbon radical of aromatic character, and their salts, processes for their manufacture, pharmaceutical preparations containing these novel compounds and their use.

Substituents of a 1,2-phenylene radical Ph can be for example lower alkyl, lower alkoxy, lower alkanoyl, halogen, trifluoromethyl and/or nitro.

The unsubstituted or substituted benzopyrone radical R can be bonded in any position and is for example a substituted or unsubstituted 2-oxo-2H-1-benzopyranyl radical which is bonded in the 4- or 6-position or, in particular, in the 3- or 7-position, or a substituted or unsubstituted 4-oxo-4H-1-benzopyranyl radical which is bonded in the 3-position or in the 6- or 7-position. Eligible substituents are, for example, aliphatic hydrocarbon radicals, free or etherified or esterified hydroxyl, acyl, substituted or unsubstituted amino and trifluoromethyl.

Aliphatic hydrocarbon radicals are for example lower alkyl or 3- or 4-membered lower alkylene which is bonded to two adjacent carbon atoms, especially in the 5,6-, 6,7- or 7,8-position or in the 3,4-position of a 2-oxo-2H-1-benzopyran-7-yl radical.

Etherified hydroxyl is for example lower alkoxy or 3- or 4-membered lower alkylenedioxy which is bonded to two adjacent carbon atoms, especially in the 5,6-, 6,7- or 7,8-position.

Esterified hydroxyl is for example hydroxyl which is esterified with a mineral acid or a carboxyl acid, such as halogen, lower alkanoyloxy or benzoyloxy which is unsubstituted or substituted by lower alkyl, lower alkoxy, halogen, trifluoromethyl and/or nitro.

Substituted amino groups are for example amino groups which are substituted by aliphatic hydrocarbon radicals, for example lower alkyl, or acyl, for example lower alkanoyl. Examples of such substituted amino groups are N-mono- or N,N-di-lower alkyleneamino or lower alkanoylamino groups.

An unsubstituted or substituted hydrocarbon radical $R_1$ of aliphatic character is for example unsubstituted or substituted lower alkyl, such as lower alkyl, hydroxy-lower alkyl or lower alkoxy-lower alkyl, lower alkenyl or phenyl-lower alkyl which is unsubstituted or substituted by lower alkyl, lower alkoxy, halogen, trifluoromethyl and/or nitro.

Acyl is for example lower alkanoyl, or benzoyl which is unsubstituted or substituted by lower alkyl, lower alkoxy, halogen and/or nitro.

Throughout this specification, the general terms employed have the following meanings:

Radicals qualified by the term "lower" contain for example not more than 7, in particular not more than 4, carbon atoms. Lower alkyl is for example methyl, ethyl, propyl, isopropyl, n-butyl, isobutyl, sec-butyl or tertbutyl, and also n-pentyl, n-hexyl, isohexyl or n-heptyl. Lower alkylene is for example 1,3-propylene, 1,4-butylene or 1,5-pentylene. Phenyl-lower alkyl is for example benzyl, 1- or 2-phenylethyl or 3-phenylpropyl. Lower alkoxy is for example methoxy, ethoxy, n-propyloxy, isopropyloxy or n-butyloxy. Lower alkoxy-lower alkyl is for example 2-ethoxyethyl, whilst hydroxy-lower alkyl denotes in particular 2-hydroxyethyl or 3-hydroxypropyl. Lower alkylenedioxy is for example 1,2-ethylenedioxy, 1,3-propylenedioxy or methylenedioxy. Lower alkanoyl is for example acetyl, propionyl, butyryl, isobutyryl, valeroyl or pivaloyl. Lower alkanoyloxy is for example acetoxy, propionyloxy, butyryloxy, isobutyryloxy, valeroyloxy or pivaloyloxy. Lower alkanoylamino is for example acetamino, propionylamino or butyrylamino. N-mono- or N,N-di-lower alkylamino is for example N-methylamino, N,N-dimethylamino or N,N-diethylamino.

The compounds of the formula I can be in the free form or in the form of their salts, in particular of their pharmaceutically acceptable non-toxic salts.

Accordingly, the compounds of the formula I can form salts with bases, such as salts of metals of groups I and II of the Periodic Table, for example alkali metal or alkaline earth metal salts, especially sodium, potassium, magnesium or calcium salts, copper or zinc salts, ammonium salts, and salts with organic bases, for example with suitable amines, for example ethylamine, triethylamine, diethylaminoethanol, ethylenediamine, benzylamine, procain, pyrrolidine, piperidine, morpholine, 1-ethylpiperidine or 2-piperidinoethanol.

The compounds of the formula I can be in a number of tautomeric forms. The most important of these tautomeric forms has the formula Ia

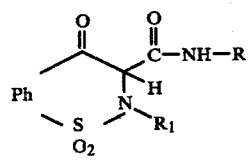

Compounds of the present invention can also be in the form of mixtures of isomers, such as racemates, or of pure isomers, for example antipodes.

The azathianaphthalene compounds of the formula I, possess valuable pharmacological, especially antiinflammatory, properties. These properties can be demonstrated when the compounds are administered perorally to rate in a dose from about 30 to 100 mg/kg to treat edema induced in the rat paw by carageen, and in a dose from about 100 to 300 mg/kg to treat edema induced in the rat paw by kaolin, and in a dose from about 30 to 100 mg/kg to treat arthritis induced in rats. The 3,4-dihydro-2H-1,2-benzothiazine 1,1-dioxides are useful as antiinflammatory agents for treating inflammatory symptoms of different etiology, in particular of the rheumatic type.

A primary object of the invention is the provision of compounds of the formula I, wherein Ph represents a 1,2-phenylene radical which is unsubstituted or substituted by lower alkyl, lower alkoxy, lower alkanoyl, halogen, nitro and/or trifluoromethyl, R represents a 2-oxo-2H-1-benzopyranyl or 4-oxo-4H-1-benzopyranyl radical which is unsubstituted or substituted by lower alkyl, lower alkoxy, halogen, lower alkanoyloxy, hydroxyl, benzoyloxy, amino which is unsubstituted or substituted by lower alkyl or lower alkanoyl, or at two adjacent carbon atoms by lower alkylene or lower alkylenedioxy, and $R_1$ represents hydrogen, lower alkyl, lower alkenyl or a phenyl-lower alkyl radical, whilst in the cited groups phenyl can be substituted by lower alkyl, lower alkoxy, halogen, trifluoromethyl and/or nitro, and salts thereof with bases.

A further object of the invention is the provision of compounds of the formula I, herein Ph represents a 1,2-phenylene radical which is unsubstituted or substituted by lower alkyl of not more than 4 carbon atoms, such as methyl, lower alkoxy of not more than 4 carbon atoms, such as methoxy or ethoxy, halogen with an atomic number up to 35, such as chlorine, nitro or trifluoromethyl, R represents a 2-oxo-2H-1-benzopyranyl radical which is bonded in the 3-, 4-, 6- or 7-position or a 4-oxo-4H-1-benzopyranyl radical which is bonded in the 3-position or in the 6-or 7-position, and which is unsubstituted or substituted by lower alkyl of not more than 4 carbon atoms, such as methyl, lower alkoxy of not more than 4 carbon atoms, such as methoxy, halogen with an atomic number up to 35, such as chlorine, lower alkanoyloxy of not more than 4 carbon atoms, such as acetoxy, hydroxyl, amino, N-mono- or N,N-di-lower alkylamino containing not more than 4 carbon atoms in the alkyl moiety, such as diemthylamino, lower alkanoylamino of not more than 4 carbon atoms, such as acetylamino, and/or at two adjacent carbon atoms by lower alkylene of not more than 4 carbon atoms, such as 1,3-propylene or 1,4-butylene, or lower alkylenedioxy of not more than 4 carbon atoms, such as methylenedioxy or 1,2-ethylenedioxy, and $R_1$ represents hydrogen or lower alkyl of not more than 4 carbon atoms, such as ethyl or methyl, and salts thereof with bases.

More particularly, it is an object of the present invention to provide compounds of the formulae Ib and Ic

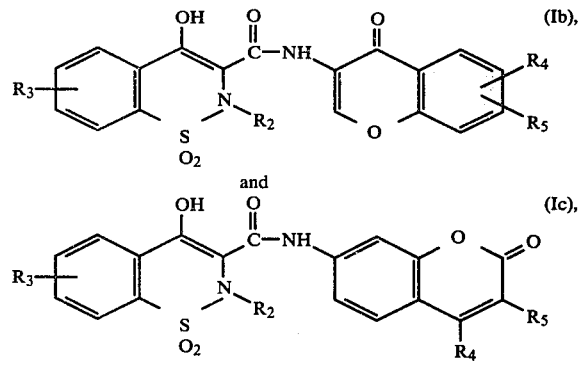

wherein $R_2$ represents hydrogen, or, in particular, lower alkyl of not more than 4 carbon atoms, for example methyl or ethyl, $R_3$ represents hydrogen, lower alkyl of not more than 4 carbon atoms, for example methyl, lower alkoxy of not more than 4 carbon atoms, for example methoxy, halogen with an atomic number up to 35, for example chlorine, trifluoromethyl or nitro, and $R_4$ and $R_5$, each independently of the other, represent hydrogen, lower alkyl of not more than 4 carbon atoms, for example methyl, or lower alkoxy of not more than 4 carbon atoms, for example methoxy, or together they represent a 3- or 4-membered lower alkylene or lower alkylenedioxy radical of not more than 4 carbon atoms which is bonded to adjacent carbon atoms, for example 1,3-propylene, 1,4-1 -butylene, methylenedioxy or 1,2-ethylenedioxy, or, in formula Ic, $R_4$ represents hydroxyl and $R_5$ represents hydrogen or lower alkyl of not more than 4 carbon atoms, such as methyl, and salts thereof with bases.

First and foremost, the invention provides compounds of the formula Ib, wherein $R_2$ represents lower alkyl of not more than 4 carbon atoms, such as methyl, $R_3$ represent hydrogen, and each of $R_4$ and $R_5$ independently represents hydrogen, lower alkyl or lower alkoxy of not more than 4 carbon atoms, such as methyl or methoxy, or together they represent 3- to 4-membered lower alkylene of not more than 4 carbon atoms which is preferably bonded in the 6,7-position, such as 1,4-propylene, and the salts thereof with bases.

Specifically, the invention provides the compounds of the formula I named in the Examples, especially those of the formula Ib, and the salts thereof with bases.

The compounds of the formula I can be obtained by methods which are known per se, for example by reacting a compound of the formula II

wherein X represents a free or functionally modified carboxyl group, or a salt thereof, with a compound of the formula

or with a reactive derivative thereof, and, if desired, converting a resulting compound into another compound of the formula I, and/or, if desired, converting a resulting salt into the free compound or into another salt, or a resulting salt into the free compound.

Functional carboxy derivatives of the formula II are preferably esters, such as lower alkyl esters, or substituted or unsubstituted phenyl esters, such as phenyl ester or 4-nitrophenyl ester or 2,4-dinitrophenyl ester, and also oligomeric, preferably dimeric, lactones, amides, such as primary amides, secondary amides, for example analides, or tertiary amides, for example 1-imidazolides, N-mono- or N,N-di-lower alkyl amides, pyrrolidides, piperidides or morpholides, and anhydrides, preferably mixed anhydrides with mineral acids, such as hydrohalic acids, for example hydrochloric acid, anhydrides with phosphinic or phosphorous acids, for example with diphenylphosphinic acid, with carboxylic acids, such as lower alkanecarboxylic acids, for example with formic or acetic acid, or with hemiesters of carbonic acid or acid esters of oxyacids of phosphorus, the remaining hydroxyl group or groups of which are esterified, for example with a lower alkanol, anhydridised, for example with a hydrohalic acid, or amidated, for example with the nitrogen atom in the 2-position of a compound of the formula II, in which $R_1$ is hydrogen. Such functional carboxy derivatives of the formula II are for example anhydrides with monophenyl or mono-lower alkyl esters of carbonic acid or di-lower alkyl esters of phosphorous acid or phosphoric acid, or cyclic anhydrides thereof, such as compounds of the formula IIa

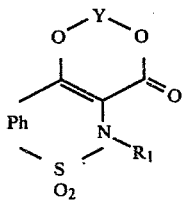

(IIa), wherein Y represents a carbonyl, thiocarbonyl or sulfinyl group or a group of the formula P—$R_o$, P(=O)—$R_o$ or P(=O) ($R_o$)$_2$, in which $R_o$ represents an organic radical, such as lower alkyl, for example methyl, or substituted or unsubstituted phenyl. Further functional carboxy derivatives of the formula II are their imino ethers (imino esters) or acid addition salts thereof, such as open-chain imino ether hydrohalides, for example imido-lower alkyl ester hydrochlorides, or cyclic imino ethers, such as corresponding 4,4- or 5,5-di-lower alkyl-4,5-dihydro-oxazoles-(2), for example 4,4-or 5,5-dimethyl-4,5-dihydro-oxazoles-(2), or 4,4,6-tri-lower alkyl-5,6-dihydro-oxazines-(2), for example 4,4,6-trimethyl-5,6-dihydro-oxazines-(2).

Reactive derivatives of amines of the formula III are in particular the amides thereof derived from hemiesters of carbonic acid or from haloformic acid or from organic sulfenic acids, such as lower alkanesulfenic acids or substituted or unsubstituted benzenesulfenic acids, for example lower alkoxycarbonyl derivatives, for example methoxycarbonyl or ethoxycarbonyl derivatives, halogencarbonyl derivatives, such as chlorocarbonyl derivatives, lower alkanesulfenyl derivatives, such as methanesulfenyl or benzenesulfenyl derivatives thereof, or corresponding carboxamides, such as lower alkanoyl, for example acetyl, derivatives.

The reaction of compounds of the formula II and III or of reactive derivatives thereof is carried out in the respective known manner.

The reaction of acids of the formula II with amines of the formula III or the salts thereof is preferably carried out in the presence of a hydrophilic agent, preferably of phosphorus pentoxide or of an ester of pyrophosphorous acid, for example tetraethylpyrophosphite, or by removing the water of reaction by distillation, preferably as an azeotrope, if necessary in an inert solvent, such as toluene, and/or at elevated temperature, for example at about 50° to 200° C.

The reaction of esters or amides or of anhydrides of acids of the formula II with amines of the formula III or the salts thereof is advantageously carried out in a solvent which is inert to the reactants, for example in toluene, xylene, tetrahydrofurane or dioxane, if necessary in the presence of a basic condensation agent, such as a tertiary organic nitrogen base, such as triethylamine or pyridine, and/or at low or elevated temperature, for example in the temperature range from about 0° C. to about 150° C.

The reaction of acids of the formula II with acyl derivatives of amines of the formula III is preferably carried out with heating, for example at about 100° to 250° C., if necessary in a solvent which is inert to the reactants, such as xylene, whilst the reaction with sulfenyl amides derived from amines of the formula III is preferably carried out at normal temperature, for example at about 0° to 50° C., preferably in an inert solvent, such as a di-lower alkyl amide, for example dimethyl formamide or N-methylpyrrolidone, in pyridine, in an ether, for example diethyl ether, dioxane or tetrahydrofurane, in benzene, toluene or xylene.

The starting materials of the formula II and III can be obtained in a manner which is known per se.

Accordingly, esters of the formula II can be obtained for example by reacting an ester of an acid of the formula IIb

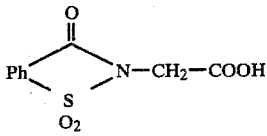

(IIb)

with one equivalent of a corresponding alkali metal alcoholate, for example sodium methanolate, preferably in dimethyl sulfoxide or dimethyl formamide. From the resulting esters it is then possible to obtain the free acids by conventional hydrolisis, and from these acids the amides thereof, for example their 1-imidazolides, by reaction with bis (1-imidazolyl)-urea, their lactones or lactames by dehydration, or their anhydrides by reaction with a dihalide, ester halide or diester of carbonic acid or thiocarbonic acid, such as phosgene, a loweralkyl ester or phenyl ester of haloformic acid, for example chloroformic acid, or thiophosgene, or a di-lower alkyl carbonate or pyrocarbonate or diphenylcarbonate or diphenylpyrocarbonate, with an ester and/or halide of a phosphinic acid of the formula ($R_o$)$_2$P—OH, such as a lower alkyl ester, for example ethyl ester, of benzenephosphinic acid, or benzenephosphinyl chloride, a diester, ester halide or dihalide of a phosphoric acid of the formula $R_o$—P(=O) (OH)$_2$, for example with benzenephosphonyl dichloride, or with thionyl chloride. Cyclic anhydrides of the formula IIa are advantageously formed in situ and reacted without isolation. Imino ethers (imino esters) of the formula II can be obtained for example by reacting a nitrile of the formula II in conventional manner, preferably by acid catalysis, with the corresponding alcohol, such as lower alkanol, phenol, amino-lower alkanol or lower alkanediol, for example with methanol, ethanol, phenol, 4-amino-2-methyl-pentan-2-ol or 2-methyl-pentane-2,4-diol. In addition, primary amides of the formula II can be obtained from the nitriles by conventional hydrolysis. Nitriles of the formula II can be obtained in a manner analogous to that described hereinbefore for obtaining the corresponding esters by starting from the nitrile of an acid of the formula IIb. N-unsubstituted esters of the formula II and corresponding nitriles can be N-substituted in conventional manner, for example with an agent which introduces the radical $R_1$.

Starting materials of the formula III can be obtained for example by conventional reduction of the nitro group to the amino group in a corresponding nitro-oxo-benzopyrane derivative, for example by treatment with hydrogen which has been catalytically activated with palladium on charcoal, for example in dimethyl formamide at normal pressure. The starting materials referred to above are in turn known or they can be prepared by methods which are in themselves known. For example, 3-nitro-4-oxo-4H-1-benzopyrane derivatives are obtained by condensing a corresponding methylsulfinylacetophenone of the formula HO—Ph—C(=O)—CH$_2$— S(=O)—CH$_3$ in the presence of a base, for example potassium carbonate in water, with a corresponding aldehyde, for example formaldehyde, eliminating methanesulfinic acid from the resulting 3-hydroxmethyl-3-methylsulfonyl-2,3-dihydro-4-oxo-4H-1-benzopyrane derivative under heat, for example in boiling toluene, and warming the 3-hydroxymethyl-4-oxo-4H-benzopyrane derivative thereby obtained with concentrated (e.g. 70%) nitric acid moderately, for example to about 40° C. A direct method of obtaining the nitro compounds consists in heating a corresponding nitroacetophenone in the presence of sodium formiate with the mixed anhydride of acetic and formic acid, for example to boiling temperature.

Reactive derivatives of amines of the formula III can be obtained in conventional manner, for example by reaction with a corresponding haloformic acid ester or carboxylic acid anhydride or by reaction with an organic disulfide, for example a di-lower alkyl disulfide, in the presence of an organic phosphorus (III) compound, for example triphenylphosphine. Carboxamides derived from 3-amino-4-oxo-4H-1-benzopyranes of the formula III can also be obtained by oximising a corresponding 4-oxo-2,3-dihydro-4H-1-benzopyrane in conventional manner, for example by reaction with isoamyl nitrite, in the 3-position and treating the resulting oxime with hydrogen in the presence of the respective carboxylic acid anhydride and of the alkali metal carboxylate corresponding thereto and of palladium on barium sulfate.

The compounds of the present invention can also be obtained by cyclising a compound of the formula IV

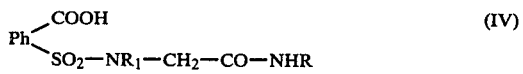

or a functional carboxy derivative and/or salt thereof to produce a compound of the formula I, and, if desired, carrying out at least one of the above additional steps.

Functional derivatives of compounds of the formula IV are, for example, esters thereof, such as lower alkyl esters or amides, such as unsubstituted or N-mono or N,N-di-lower alkyl amides or anilides, and also lactames derived from compounds of the formula IV, in which $R_1$ is hydrogen, and which are in dynamic equilibrium to these or to their esters and amides, for example those of the formula

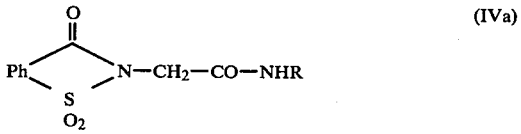

Salts of compounds of the formula IV are in particular the metal or ammonium salts thereof, in particular alkali metal salts, for example sodium or potassium salts or ammonium salts.

The cyclisation of compounds of the formula IV or their functional derivatives and/or salts to produce compounds of the formula I is carried out in conventional manner, for example by treatment with a basic condensation agent. Suitable condensation agents are in particular metal bases, such as alkali metal alcoholates, especially sodium or potassium lower alkanolates, for example sodium methanolate or sodium ethanolate or potassium tert-butylate, alkali metal amide, for example sodium amide or lithium diisopropylamide, or alkali metal or alkaline earth metal hydrides, for example sodium or potassium hydride. The ring expanding cyclisation of compounds of the formula IVa, for which at least two equivalents of the basic condensation agent are required, can furthermore be carried out in the presence of organic nitrogen bases, preferably tertiary amines, such as triethylamine, pyridine or quinoline, or of alkali metal hydroxides or ammonium hydroxides, for example potassium, sodium or ammonium hydroxide. The reaction is carried out, if desired, in the presence of a solvent or diluent, if necessary with cooling or heating, for example in the temperature range from about 0° to about 150° C., in a closed vessel and/or in an inert gas, such as nitogen.

The choice of solvent is determined in particular by the condensation agent to be employed. When treatment with an alkali metal alcoholate is carried out, the corresponding alcohol is preferably used, whereas the treatment with an alkali metal amide or an alkali metal or alkaline earth metal hydride is preferably carried out in a N,N-di-lower alkyl-lower alkanoylamide, such as dimethyl formamide, or a di-lower alkyl sulfoxide, such as dimethyl sulfoxide, and the treatment with an organic nitrogen base is carried out preferably in an excess thereof, and the treatment with an alkali metal hydroxide or ammonium hydroxide is carried out preferably in an aqueous solution, for example in water, ethanol/water or dimethyl formamide/water.

The starting materials of the formula IV and the functional carboxy derivatives thereof are known or they can be obtained by methods which are in themselves known.

Compounds of the formula IVa can be obtained for example by converting a compound of the formula IVb

in conventional manner, for example in analogy to the formation of saccharin sodium, into a metal salt, and reacting this latter with a compound of the formula Hal—Ch$_2$—CO—NHR, in which "Hal" represents chlorine or bromine.

Compounds of the formula IV or the esters and amides thereof can be obtained from the compounds of the formula IVa by conventional reaction with one equivalent of an alkali metal hydroxide, alkali metal alcoholate or amine.

The compounds of the present invention can furthermore be obtained by intramolecular cyclisation of a compound of the formula V

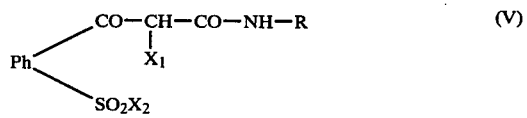

wherein one of the symbols $X_1$ and $X_2$ represents a group of the formula —NHR$_1$ and the other represents a free or etherified or reactive esterified hydroxyl group or amino group $X_3$, and, if desired, carrying out one or more of the above additional operations.

Etherified hydroxyl groups are for example etherified with a lower alkanol. Reactive esterified hydroxyl groups are preferably halogen atoms, such as chlorine, bromine or iodine atoms. Amino is for example an amino group of the formula —NHR$_1$.

The intramolecular cyclisation of compounds of the formula V is carried out in conventional manner, for example by removing the compound of the formula HX$_3$ which is split off in the course of the reaction, in an appropriate manner, for example by physical or chemical means, from the reaction mixture, for example by heating in a solvent or diluent having a boiling point higher than that of the eliminated compound HX$_3$ or which forms an azeotropic mixture with this compound, or by chemical bonding as a salt, preferably an acid addition salt. It is thus possible to remove water, alcohols and low molecular amines by distillation. Hydrohalic acids can furthermore be bound by basic condensation agents, such as hydroxides, carbonates or hydrogen carbonates of alkali metals, for example sodium hydroxide, potassium carbonate or sodium carbonate, or organic nitrogen bases, such as tertiary amines, for example triethylamine, pyridine or quinoline, in the form of acid addition salts, and water can be bound by a hydrophilic agent, such as dicyclohexylcarbodiimide. The above reaction is carried out in conventional manner in the presence or absence of a solvent or diluent, if necessary with heating, for example in the temperature range from about 20° to 180° C., in a closed vessel and/or in an inert gas, such as nitrogen.

The starting materials are known or they can be obtained in a manner known per se, for example by reacting a compound of the formula Va

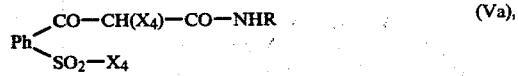

wherein at least one of the substituents X$_4$ represents halogen, for example chlorine, and a substituent X$_4$ which is different from halogen represents a group —NHR$_1$, with a compound of the formula R$_1$NH$_2$.

The intermediates of the formula Va can be obtained, for example, by condensing an ester of a corresponding compound of the formula Ph(SO$_2$NHR$_1$)—COOH, obtainable by treatment of the corresponding saccharin compound with potassium hydroxide and usual esterification at the carboxyl group, or an ester of a corrresponding compound of the formula Ph(SO$_2$Cl)—COOH, obtainable by conventional oxidation of the corresponding o-toluenesulfonic acid to the o-sulfobenzoic acid, esterification thereof at the carboxyl group and chlorination of the sulfo group, for example with phosphoroxy chloride, in conventional manner with an amide of the formula CH$_3$—CO—NHR, and halogenating the resulting β-keto acid amide in the α-position, for example with phosphorus pentachloride or sulfuryl chloride. If desired, other intermediates of the formula VIIa can be obtained by reaction with a compound of the formula HX$_3$ which is different from hydrogen halide.

The compounds of the present invention can finally be obtained by converting a radial X$_5$ into hydroxyl in a compound of the formula VI

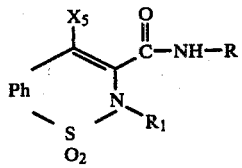

wherein X$_5$ represents a radical which can be converted into hydroxyl, and, if desired, carrying out one or more of the above additional operations.

Radicals X$_5$ which can be converted into hydroxyl are for example etherified or esterified hydroxyl groups, substituted or unsubstituted amino or mercapto groups, sulfinyl or sulfonyl groups or carboxyl.

Etherified hydroxyl groups are for example hydroxyl groups which are etherified with an aliphatic, araliphatic or aromatic alcohol, such as lower alkoxy or substituted or unsubstituted phenoxy or benzyloxy groups.

Esterified hydroxyl groups are for example hydroxyl groups which are esterified with a hydrohalic acid or with a carboxylic or organic sulfonic acid, such as lower alkanoyloxy, substituted or unsubstituted benzoyloxy, lower alkanesulfonyloxyn or lower alkenesulfonyloxy, for example methanesulfonyloxy, ethanesulfonyloxy or ethenesulfonyloxy or substituted or unsubstituted benzenesulfonyloxy, and also halogen, for example chlorine or bromine.

Substituted amino groups are for example amino groups which are substituted by substituted or unsubstituted phenyl groups, lower alkyl, lower alkylene or azaalkylene, oxaalkylene or thiaalkylene containing not more than 7 chain members, such as substituted or unsubstituted anilino, N-mono or N,N-di-lower alkylamino or 5- to 7- membered 3-aza-, 3-oxa- or 3-thiaalkylene amino, for example pyrrolidino, piperidino or morpholino. Further substituted amino groups X$_5$ are diazonium groups, for example diazonium halide or tetrafluoroborate groups, or electronegatively monosubstituted amino groups, such as hydroxylamino, unsubstituted or phenylated hydrazino, acylamino, such as lower alkanoylamino, for example acetylamino or benzoylamino groups, sulfonylamino, such as sulfonylamino groups derived from aliphatic or aromatic sulfonic acids, for example methanesulfonylamino, benzenesulfonylamino, 4-toluenesulfonylamino or 4-bromosulfonylamino.

Substituted mercapto groups are for example mercapto groups which are substituted for example by aliphatic, cycloaliphatic or aromatic hydrocarbon radicals, such as lower alkylthio, for example methylthio or ethylthio, cycloalkylthio groups, for example cyclohexylthio or phenylthio groups.

Sulfonyl and sulfinyl groups are respectively for example fluorosulfonyl and fluorosulfinyl or aliphatic or aromatic sulfonyl and sulfinyl groups, such as lower alkanesulfonyl, for example methanesulfonyl or ethanesulfonyl, lower alkanesulfinyl, for example methanesulfinyl or ethanesulfinyl, lower alkenesulfonyl, for example ethenesulfonyl, or benzenesulfonyl and benzenesulfinyl groups.

In the above groups X$_5$, phenyl radicals can be substituted for example by lower alkyl, such as methyl, lower alkoxy, such as methoxy, halogen, such as chlorine or bromine, and/or nitro.

The conversion of compounds of the formula VI into compounds of the formula I is carried out in conventional manner, for example by hydrolysis.

The hydrolysis can be carried out in conventional manner, for example in the presence of a preferably basic hydrolysing agent, for example sodium or potassium hydroxide, at normal or, if necessary, elevated, temperature, for example in the temperature range from about 20° to about 120° C., if desired in the presence of a solvent and/or other assistants. Suitable solvents are in particular watermiscible solvents, such as lower alkanols, for example methanol or ethanol, ethers, such as dioxane, di-lower alkyl carboxamides, such as dimethyl formamide, sulfoxides, such as dimethyl sulfoxide, and nitrogen bases, such as pyridine. Further assistants are for example monovalent copper compounds for the hydrolysis of carboxyl to hydroxyl, for example copper (I) chloride, or copper (II) compounds, for example copper oxide, together with metallic copper.

The starting compounds are known or they can be obtained by methods which are known per se, for example by reacting a compound of the formula VIa

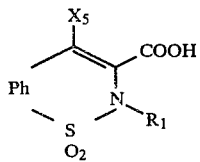

(VIa)

or a functional carboxy derivative thereof, such as an ester, for example a lower alkyl ester, or an anhydride thereof, such as the chloride, in conventional manner with one equivalent of an amine of the formula R—NH$_2$ (III).

Intermediates of the formula VI, wherein X$_5$ is chlorine, can also be obtained by esterifying an acid of the formula VIb

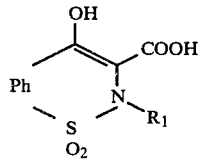

(VIb)

or a functional derivative thereof, for example a lower alkyl ester, by reaction with a chlorinating agent, for example thionyl chloride, phosphorus trichloride, phosphoroxy chloride or phosphorus pentachloride, at the 4-hydroxyl group, and, if desired, anhydridising at the carboxyl group with hydrochloric acid.

The corresponding compounds of the formula VI, in which X$_5$ is a substituted or unsubstituted mercapto group, can be obtained from the above chlorine compounds in analogous manner, for example by reaction with thiourea or a salt of an alkali metal alkanethiocarboxylic acid, for example with sodium thiolacetate, and subsequent hydrolysis, or by reaction with an alkali metal salt, such as the sodium salt, of a mercaptan. From the mercaptans it is possible to obtain the corresponding sulfonyl or sulfinyl compounds by treatment with a conventional S-oxidising agent, for example 3-chloroperbenzoic acid. Compounds of the formula VI, wherein X$_5$ is etherified or esterified hydroxyl or amino which is unsubstituted or substituted by substituents other than electronegative substituents, can be obtained in analogous manner by reaction with the corresponding alcohol or the corresponding carboxylic acid or with an alkali metal thereof, for example the sodium salt, or with ammonia or a corresponding amine. The primary amino group X$_5$ can then be electronegatively substituted by reaction with an agent which introduces an electronegative substituent, for example with a carboxylic acid anhydride or halide or a sulfonic acid halide or by conventional diazotisation. The above reciprocal conversions of groups X$_5$ can be carried out with compounds of the formulae VI or VIa or, in the latter case, with the esters thereof.

Starting materials of the formula VI, wherein X$_5$ is etherified hydroxyl, can furthermore be obtained by etherifying an acid of the above formula VIb or an ester thereof at the alcoholic and at a carboxylic hydroxyl group which may be present, for example with a lower alkyl halide or dilower alkyl sulfate, in the presence of potassium carbonate in acetone or amyl alcohol, and reacting the resulting ester in conventional manner, if necessary after hydrolysis to the acid and/or chlorination thereof, for example with thionyl chloride, with an amine of the formula III.

Starting materials of the formula VI, wherein X$_5$ represents a disubstituted amino group, can furthermore be obtained by converting a compound of the formula VIc

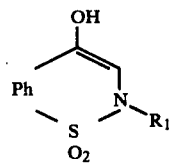

(VIc)

initially by reaction with the corresponding amine into the enamine, reacting this latter in the presence of triethylamine with phosgene and subsequently reacting the enamine acid chloride in conventional manner with an amine of the formula R-NH$_2$ (III).

The compounds of the formula I can also be obtained by cyclising R' to the radical R in a compound of the formula VII

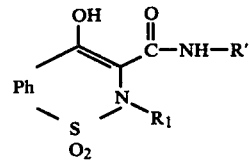

(VII), wherein R' represents a radical which can be cyclised to the substituted or unsubstituted benzopyrone radical R, or in a salt thereof, and, if desired, converting a compound so obtained into another compound of the formula I and/or a resulting free compound into a salt or a resulting salt into the free compound or into another salt.

Radicals R' which can be cyclised to benzopyrone radicals R are for example radicals of the formulae VIII, VII-2. VII-3 or VIIa-4

—CH$_2$—C(=O)—Ph—O—C(=O)—R$_6$      (VIIa-1),

—CH(COR$_6$)—C(=O)—Ph—R$_8$      (VIIa-2),

—C(=O)—CH(R$_6$)—C(=O)—Ph—R$_8$      (VIIa-3)

or

—C(R$_9$)=C(R$_6$)—O—Ph—H  (VIIa-4), which can be cyclised to radicals R of the formula VIIa

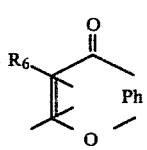
(VIIa)

radicals of the formulae VIIb-1, VIIb-2 or VIIb-3

—Ph$<$ $\begin{array}{l}$C(=O)—CH$_2$R$_6$\\O—C(=O)—R$_7$\end{array}$  (VIIb1),

—Ph$<$ $\begin{array}{l}$C(=O)—CH(R$_6$)—C(=O)—R$_7$\\R$_8$\end{array}$  (VIIb2)

—Ph$<$ $\begin{array}{l}$H\\O—C(R$_7$)=C(R$_6$)—R$_9$\end{array}$  (VIIb3), which can be cyclised to radicals of the formula VIIb

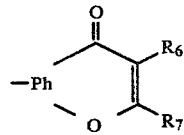
(VIIb), radicals of the formulae VIIc-1, VIIc-2, VIIc-3 or VIIc-4

—C(R$_9$)=C(R$_7$)—Ph—R$_8$  (VIIc1),

—C(PhR$_8$)=C(R$_7$)—R$_9$  (VIIc2),

—CH$_2$—C(=O)—O—Ph—R$_9$  (VIIc3), or

—CH(R$_9$)—C(=O)—Ph—R$_8$  (VIIc4)

which can be cyclised to radicals of the formula VIIc

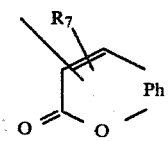
(VIIc)

or radicals of the formulae VIId-1, VIId-2, VIId-3 or VIId-4

—Ph(R$_8$)—C(R$_7$)=C(R$_6$)—R$_9$  (VIId-1),

—Ph(R$_9$)—O—C(=O)—CH$_2$R$_6$  (VIId-2),

—Ph(R$_8$)—C(=O)—CH(R$_6$)—R$_9$  (VIId-3)

or

—Ph(O—R$_9$)—C(=O)—CH$_2$R$_6$  (VIId-4), which can be cyclised to radicals of the formula VIId

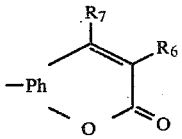
(VIId)

wherein Ph is as defined at the outset, R$_6$ represents hydrogen, an aliphatic hydrocarbon radical or a substituted or unsubstituted phenyl or pyridyl radical, R$_7$ has one of the meanings assigned to R$_6$ or represents hydroxyl or together with R$_6$ represents a divalent aliphatic hydrocarbon radical, R$_8$ represents free or etherified hydroxyl or hydroxyl which is esterified with a carboxylic acid, and R$_9$ represents free or esterified or anhydridised carboxyl.

Aliphatic hydrocarbon radicals R$_6$ and R$_7$ are in particular lower alkyl radicals. Possible substituents of phenyl radicals R$_6$ and R$_7$ are for example lower alkyl, lower alkoxy, halogen and/or nitro, and of pyridyl radicals R$_6$ and R$_7$, in particular lower alkyl. Divalent aliphatic radicals R$_6$ and R$_7$ are in particular 3- to 5-membered alkylene radicals, such as 1,3-propylene and 1,4-butylene. Etherified hydroxyl is for example lower alkoxy, such as methoxy, or phenoxy which can be substituted or unsubstituted as in the case of R$_6$ and R$_7$ as phenyl. Hydroxyl esterified with a carboxylic acid is for example lower alkanoyloxy, such as formyloxy or acetoxy, or benzoyloxy which can be substituted or unsubstituted as in the case of R$_6$ and R$_7$ as phenyl. Esterified carboxyl is for example lower alkoxycarbonyl, such as methoxycarbonyl or ethoxycarbonyl, or phenoxycarbonyl which can be substituted or unsubstituted as in the case of R$_6$ and R$_7$ as phenyl. Anhydridised carboxyl is for example lower alkanoyloxycarbonyl, such as formylcarbonyl or acetoxycarbonyl, or halocarbonyl, such as chlorocarbonyl.

The cyclisation of compounds of the formula VII is carried out in conventional manner, for example in that known from the chemical literature for analogous reactions, preferably in the presence of a basic or acid condensation agent and in a solvent which is inert to the reactants, if necessary accompanied by the removal of volatile compounds formed during the reaction, for example by azeotropic distillation, with cooling or heating, for example in the temperature range from about 0° to about 200° C., in an inert gas, such as nitrogen, and/or in a closed vessel. Basic condensation agents are for example hydroxides, alcoholates, such as lower alcoholates, carbonates or carboxylates, such as lower alkanoic acid carboxylates, of alkali metals, for example sodium or potassium hydroxide, sodium or potassium methanolate or sodium or potassium ethanolate, potassium carbonate or sodium or potassium acetate. Examples of acid condensation agents are proton acids or their anhydrides, such as sulfuric acid, phosphoric acid, hydrohalic acids, for example hydrochloric, hydrobromic or hydriodic acid, phosphorus pentoxide or acetyl chloride or acetic anhydride, and Lewis acids, such as aluminium trichloride. Examples of suitable solvents are hydrocarbons, such as benzene, toluene or xylene, alcohols, such as lower alkanols or lower alkanediols, for example ethanol, methanol or ethylene glycol, di-lower alkyl ketones, such as acetone, aliphatic or cycloaliphatic ethers, such as tetrahydrofurane or dibutyl ethers, carboxylic acids, such as acetic acid, or the anhydrides thereof, such as acetic anhydride, or tertiary lower alkanoic acids amides, such as dimethyl formamide or N-methylpyrrolidone, or mixtures, for example aqueous mixtures thereof. For cyclising compounds of the formula VII, wherein R' represents a radical of the formula VIIa-2, VIIa-3, VIIa-4, VIIb-2, VIIb-3, VIIc-1, VIIc-2, VIIc-4, VIId-1 or VIId-3, preferably acid condensation agents are used, such as strong (e.g. at least 20%) aqueous hydriodic acid or hydrobromic acid in acetic acid, and, where R' represents a radical of the formula VIIc-4 or VIId-3, for example concentrated (i.e. at least 50%) sulfuric acid, and, where R' represents a radical of the formula VIIa-4 or VIIb-3, for example also sulfuric acid, but also acid anhydrides, for example phosphorus pentoxide or acetyl chloride. Starting from compounds of the formulae VIIa-1, VIIb-1, VIIc-3, VIIc-4, the reaction is preferably carried out in the presence of a basic condensation agent, for example potassium carbonate in acetone or a sodium or potassium salt of an organic carboxylic acid in the presence of the volatile anhydride thereof, where R' is a radical of the formula VIIa-1 or VIIb-1; or sodium or an alkali metal alcoholate, preferably sodium alcoholate, in the respective alcohol, where R' is a radical of the formula VIIc-3, VIIc-4, VIId-3 or VIId-4.

Where they are novel, the starting materials of the formula VII can be obtained by methods which are known per se, for example by reacting an ester, such as ester, of an acid of the formula

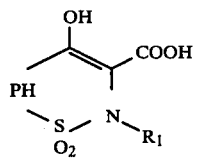

(VIII)

with an amine of the formula R'—NH$_2$, preferably in accordance with the procedure described for the reaction of esters of the formula II with amines of the formula III.

Compounds of the formula VII, in which R' represents a radical of the formula VIIa-2, can furthermore be obtained by reacting for example compounds of the formula IX

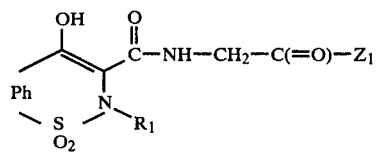

(IX)

in the presence of the mixed anhydride of formic acid and acetic acid, with a salt, for example the sodium salt, of an acid of the formula

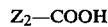

Z$_2$—COOH (X), one of Z$_1$ and Z$_2$ being a group R$_6$ and the other a group —PhR$_8$. In analogous manner, compounds of the formula VII, in which R' represents a radical of the formula VIIb-2, can be obtained by reacting an acid of the formula XI

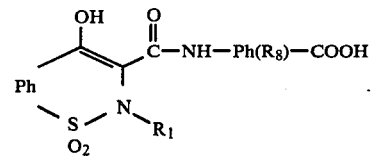

(XI)

or an ester thereof, for example a lower alkyl ester, or a salt thereof, for example the sodium salt, with a compound of the formula

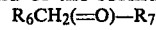

R$_6$CH$_2$(=O)—R$_7$ (XII)

or an ester and/or salt thereof, for example the sodium salt, for example as described hereinbefore or in the presence of sodium in xylene or of sodium methanolate in methanol. Compounds of the formula VII, in which R' represents a radical of the formula VIIb-3, can be obtained by reacting the alkali metal phenolate, for example sodium phenolate, derived from a compound of the formula XIII

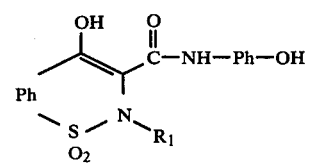

(XIII)

with a compound of the formula XIV

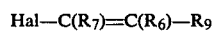

Hal—C(R$_7$)=C(R$_6$)—R$_9$ (XIV)

wherein Hal represents halogen, for example chlorine or bromine, or preferably with a salt or ester thereof, for example a lower alkyl ester. Compounds of the formula VII containing as radical R' a group of the formula VIId-1 can be obtained by reacting a compound of the formula XVI

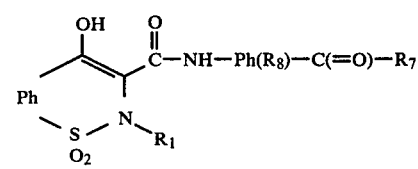

(XVI)

with a compound of the formula

R$_6$CH$_2$R$_9$ (XVII)

in conventional manner.

Starting materials of the formula VII, wherein R' represents a radical of the formulae VIIa-1, VIIb-1, VIIc-4, VIIc-4, VIId-3 or VIId-4 are advantageously prepared in situ under the reaction conditions and cyclised without isolation. Accordingly, for example, a compound of the formula XVIII

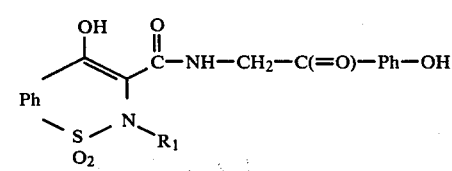

(XVIII)

can be reacted with an anhydride of an acid of the formula

$$R_6COOH \quad\quad (XIX)$$

advantageously in the presence of an alkali metal salt thereof, for example the sodium salt, whereupon a compound of the formula VII is formed as intermediate, in which R' represents a radical of the formula VIIa-1. In analogous manner, a compound of the formula XX

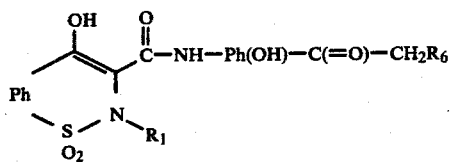
(XX)

can be reacted with an anhydride of a compound of the formula

$$R_7COOH \quad\quad (XXI)$$

wherein $R_7$ is different from hydroxyl, to form a compound of the formula VII as intermediate, wherein R' represents a group of the formula VIIb-1. In addition, it is possible in the presence of a strong base, for example sodium, or of an alkali metal alcoholate, for example a sodium alcoholate, to condense compounds of the formulae XXII

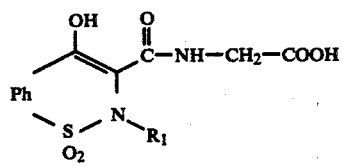
(XXII)

or an ester or a salt thereof, and

$$HO-Ph-R_9 \quad\quad (XXIII)$$

or a salt thereof, to form a radical R' of the formula VIIC-3 as intermediate, or to condense compounds of the formulae

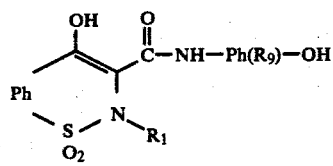
(XXIV)

or an ester and/or a salt thereof, and
$$R_6CH_2COOH \quad\quad (XXV)$$

or an ester or a salt thereof, to form a radical R' of the formula VIId-1 as intermediate, or to condense compounds of the formulae

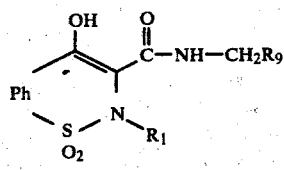
(XXVI)

or an ester and/or a salt thereof, and

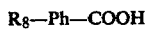
$$R_8-Ph-COOH \quad\quad (XXVII)$$

or an ester or a salt thereof, to form a radical R' of the formula VIIc-4 as intermediate, or to condense compounds of the formulae XXVIII

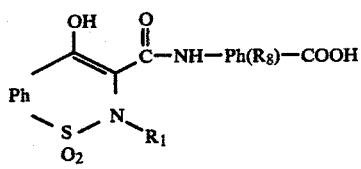
(XXVIII)

or an ester and/or a salt thereof, and $$R_6CH_2R_9 \quad\quad (XXIX)$$

or an ester or a salt thereof, to form a radical R' of the formula VIId-3 as intermediate. Furthermore, it is possible to react in advantageous manner a compound of the formula XXX

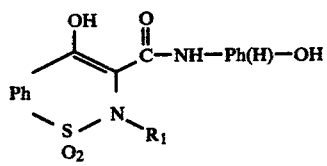
XXX with a compound of the formula

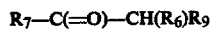
$$R_7-C(=O)-CH(R_6)R_9 \quad\quad (XXXI)$$

in the presence of an acid, for example a proton acid, for example sulfuric acid, or of an acid anhydride, for example phosphorus pentoxide. In this reaction, which yields the corresponding benzopyrone derivatives of the formula I direct accompanied by the formation of a not precisely known intermediate as initial isolatable reaction product, the ratio of the resulting 2H-1-benzopyrone and 4H-1-benzopyrone compound is determined by the specific starting materials and the reaction conditions. In general, however, 4H-1-benzopyrone derivatives are primarily obtained when using phosphorus pentoxide as condensation agent, whilst 2H-1-benzopyrone derivatives are primarily obtained when using more or less concentrated sulfuric acid.

A resulting compound of the formula I can be converted in conventional manner into another compound of the formula I.

For example, a substituted or unsubstituted hydrocarbon radical of aliphatic character can be introduced into a compound of the formula I, wherein $R_1$ represents hydrogen, for example by reaction with an agent which introduces such a radical, such as a reactive ester, for example a mineral acid or sulfonic acid ester, of the respective alcohol, or with an epoxide derived therefrom. Mineral acid esters are in particular esters of hydrohalic acids, such as esters of hydrochloric, hydrobromic or hydriodic acid, and also sulfuric acid and sulfonic acid esters, especially esters of aromatic or aliphatic sulfonic acids, such as esters of methanesulfonic, ethanesulfonic, benzenesulfonic, p-bromobenzenesulfonic or p-toluenesulfonic acid. Epoxides are for example those derived from lower alkyl or phenyl-lower alkyl radicals $R_1$ containing at least two carbon atoms in the alkyl moiety. In analogous manner, it is also possible to etherify primary amino and hydroxyl as substituents of R by aliphatic hydrocarbon radicals or to etherify hydroxyl at 1,2-phenylene radicals Ph by lower alkyl.

Furthermore, primary amino and/or hydroxyl in the radical R can be acylated in analogous manner, for example by reaction with a carboxylic acid anhydride, such as a lower alkanoic acid anhydride or substituted or unsubstituted benzoic acid anhydride or with a corresponding halide, such as the chloride.

The above reactions are carried out in conventional manner, if necessary in the presence of a basic condensation agent, such as a metal base, for example a hydroxide, carbonate or hydride of an alkali metal or alkaline earth metal, or an alkali metal hydrocarbon compound, a nitrogen base, for example a tertiary amine, if necessary in an inert solvent and/or with cooling or heating, for example in the temperature range from about −10° to about +105° C. Metal bases are in particular sodium and potassium hydroxide or sodium or potassium carbonate, sodium methanolate, sodium hydride, diisopropylamine lithium and phenyl and butyl lithium. Nitrogen bases are in particular pyridine, triethylamine or quinoline.

Conversely, in compounds of the present invention it is possible to hydrolyse in conventional manner acylamino to amino and/or acyloxy and/or etherified hydroxyl to hydroxyl, for example in the presence of an acid or basic hydrolysing agent, if necessary with gentle heating, for example in the temperature range from about 10° to about 100° C., to produce the corresponding amino or hydroxy compounds of the formula I. Acid hydrolysing agents are in particular mineral acids, such as hydrochloric acid or sulfuric acid, organic carboxylic or sulfonic acids, such as acetic acid or p-toluenesulfonic acid. Basic hydrolysing agents are in particular alkalies, such as sodium or potassium hydroxide or sodium or potassium carbonate. Mineral acid hydrolysing agents for the hydrolysis of etherified hydroxyl groups are also hydrobromic acid in acetic acid, hydrochloric acid in pyridine or hydriodic acid.

The above reactions are carried out in conventional manner in the presence or absence of diluents, condensation agents and/or catalysts, if necessary at low or elevated temperature, in a closed vessel and/or in an inert gas atmosphere.

Depending on the process conditions and the starting materials, the final products having salt-forming properties are obtained in the free form or in the form of their salts, which can be converted into each other or into other salts in conventional manner. Thus the compounds of the formula I can be obtained in the form of their salts with bases, and these salts can be converted in conventional manner, for example by reaction of the free compound with a corresponding base, such as a hydroxide of a metal of Groups I and II of the Periodic Table, for example a hydroxide, carbonate, hydrogen carbonate, amide or hydride of an alkali metal or alkaline earth metal, or a suitable alkali metal lower alkanolate, or with copper or zinc oxide, or with ammonia or an amine, into a salt, especially into a pharmaceutically acceptable salt. Free compounds of the formula I can be literated from corresponding salts in conventional manner, for example by reaction with acids.

These and other salts can be used for purifying the compounds of the invention, for example by converting the free compounds into their salts, isolating these latter and converting them again into the free compounds. Because of the close relationship between the compounds of the invention in the free form and in the form of their salts, what is stated in this specification in respect of the free compounds also applies by analogy to the corresponding salts.

Resulting isomer mixtures can be separated on the basis of the physico-chemical differences of the constituents in known manner into the two stereoisomers or pure isomers, for example by chromatography and/or fractional crystallisation. Advantageously, the isomer which possesses the pharmacologically more valuable properties is isolated.

The invention also relates to those embodiments of the process in which a compound obtainable as an intermediate in any stage of the process is used as starting material and the missing steps are carried out, or in which a starting material is formed under the reaction conditions, or in which a reaction component is used, if desired, in the form of its derivatives, such as its salts and/or in the form of isomer mixtures or an isomer.

For carrying out the reactions of the present invention it is advantageous to use those starting materials which result in the groups of final products particularly referred to at the outset and, in particular, in the final products specifically described or singled out for special mention.

The pharmaceutical preparations of the present invention which contain compounds of the formula I, or pharmaceutically acceptable salts of such compounds having salt-forming groups, are preparations for enteral, such as oral or rectal, administration, and also parenteral administration, to warm-blooded animals, and contain the pharmacologically active substance by itself or together with a pharmaceutically acceptable carrier. They contain from about 10% to about 95%, preferably from about 20% to about 90%, of the active substance.

The pharmaceutical preparations of the present invention are prepared in a manner known per se, for example by conventional mixing, granulating, sugar-coating, dissolving and lyophilising methods. Pharmaceutical preparations which are suitable for oral administration can be obtained by combining the active ingredient with solid carriers, if appropriate granulating the mixture thereby obtained, and processing the mixture or granules, if desired or necessary after the addition of suitable adjuncts, to tablets or sugar-coated tablet cores.

Suitable carriers are in particular fillers, such as sugar, for example, lactose, saccharose, mannitol or sorbitol, cellulose preparations and/or calcium phosphates, e.g. tricalcium phosphate or calcium hydrogen phosphate, also binders such as starch pastes, for example maize, corn, rice or potato starch paste, gelatin, tragacanth, methyl cellulose, hydroxypropylmethylcellulose, sodium carboxymethylcellulose and/or polyvinylpyrrolidone, and/or, if desired, disintegrators, such as the above starches, also carboxymethyl starch, crosslinked polyvinylpyrrolidone, agar, alginic acid or a salt thereof, such as sodium alginate. Adjuncts are chiefly glidants and lubricants, for example, silicic acid, talc, stearic acid or salts thereof, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet cores, for example to identify or indicate different doses of active ingredient.

Further pharmaceutical preparations for oral administration are dry-filled capsules, and also soft sealed capsules made from gelatin and a plasticiser, such as glycerin or sorbitol. The dry-filled capsules can contain the active ingredient in the form of granules, for example in admixture with fillers such as maize starch, binders and/or lubricants, such as talc or magnesium stearate, and optionally stabilisers. In soft capsules, the active ingredient is preferably dissolved or suspended in suitable liquids, for example in fatty oils, paraffin oil or liquid polyethylene glycols, to which stabilisers can also be added.

Preparations suitable for parenteral administration are, in particular, aqueous solutions of an active ingredient in the water-soluble form, for example of a water-soluble salt, and also suspensions of the active ingredient, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

The compounds of the present invention of the formula I, or the pharmaceutically acceptable salts thereof, can be used as pharmacologically active substances, especially as antiphlogistic agents, and as analgesics, preferably in the form of pharmaceutical preparations. The dosage of the active substance depends on the species of warm-blooded animal, the body weight, age, individual condition, and on the mode of application. On average, a daily dose of about 50 to about 200 mg, preferably from about 75 to about 150 mg, will be administered to a warm-blooded animal having a body weight of about 70 kg.

The following Examples illustrate the invention, but are not to be regarded as limiting it in any way.

EXAMPLE 1

A 500 ml round flask, which is connected to a distillation head and a condenser, is charged with 3.5 g (0.013 mole) of 2-methyl-3,4-dihydro-4-oxo-2H-1,2-benzothiazine-3-carboxylic acid methyl ester 1,1-dioxide, 2.1 g (0.013 mole) of 3-amino-4-oxo-4H-1-benzopyrane and 100 ml of dry xylene. Then nitrogen gas is blown into the resulting suspension for 5 minutes. The reaction mixture is subsequently subjected to a slow distillation lasting 15 hours, in the course of which procedure complete solution is attained after heating for only 10 minutes. The solvent is replaced every 2 hours. The reaction mixture is then cooled to 50° C. The precipitate which has formed is collected by filtration, washed with ethanol and dried, yielding 2-methyl-3,4-dihydro-4-oxo-N-(4-oxo-4H-1-benzopyran-3-yl)-2H-1,2-benzothiazine-3-carboxamide, 1,1-dioxide in the form of brownish crystals with a melting point of 290° C. (with decomp.).

EXAMPLE 2

The following compounds can also be prepared by the process of Example 1:

2-methyl-3,4-dihydro-4-oxo-N-(4,6,7,8-tetrahydro-4-oxo-cyclopenta[g]-1-benzopyran-3-yl)-2H-1,2-benzothiazine-3-carboxamide 1,1-dioxide, mp. 293°–295° C., 2-methyl-3,4-dihydro-4-oxo-N-(4-oxo-6-methyl-4H-1-benzopyran-3-yl)-2H-1,2-benzothiazine-3-carboxamide 1,1-dioxide, mp. 272°–275° C., 2-methyl-3,4-dihydro-4-oxo-N-(4-oxo-8-methyl-4H-1-benzopyran-3-yl)-2H-1,2-benzothiazine-3-carboxamide 1,1-dioxide, mp. 303°–305° C., 2-methyl-3,4-dihydro-4-oxo-N-(2-oxo-4-hydroxy-6-methyl-2H-1-benzopyran-3-yl)-2H-1,2-benzothiazine-3-carboxamide 1,1-dioxide, m.p. 279° C. (decomp.), 2-methyl-3,4-dihydro-4-oxo-N-(4-oxo-6-chlor-8-methyl-4H-1-benzopyran-3-yl)-2H-1,2-benzothiazine-3-carboxamide 1,1-dioxide, m.p. 292°–295° C., 2-methyl-3,4-dihydro-4-oxo-N-(4-oxo-6,7-dimethyl-4H-1-benzopyran-3-yl)-2H-1,2-benzothiazine-3-carboxamide 1-dioxide, m.p. 292°–297° C., 2-methyl-3,4-dihydro-4-oxo-N-(4-oxo-6-methoxy-4H-1-benzopyran-3-yl)-2H-1,2-benzothiazine-3-carboxamide 1,1-dioxide, m.p. 272°–276° C., 2-methyl-3,4-dihydro-4-oxo-N-(4-oxo-5,7-dimethyl-4H-1-benzopyran-3-yl)-2H-1,2-benzothiazine-3-carboxamide 1,1-dioxide, m.p. 286°–291° C. (decomp.), 2-methyl-3,4-dihydro-4-oxo-N-(2-oxo-4-hydroxy-6-chlor-2H-1-benzopyran-3-yl)-2H-1,2-benzothiazine-3-carboxamide 1,1-dioxide, 2-methyl-3,4-dihydro-3-oxo-N-(2-oxo-4-hydroxy-6,8-dichlor-2H-1-benzopyran-3-yl)-2H-1,2-benzothiazine-3-carboxamide 1,1-dioxide, 2-methyl-3,4-dihydro-4-oxo-N-(2-oxo-4-hydroxy-4,6,7,8-tetrahydro-cyclopenta[g]-2H-1-benzopyran-3-yl)-2H-1,2-benzothiazine-3-carboxamide 1,1-dioxide and 2-methyl-3,4-dihydro-4-oxo-N-(2-oxo-4-hydroxy-8-methyl-2H-1-benzopyran-3-yl)-2H-1,2-benzothiazine-3-carboxamide 1,1-dioxide.

EXAMPLE 3

8.1 g of 2-methyl-3,4-dihydro-4-oxo-2H-1,2-benzothiazine-3-carboxylic acid methyl ester 1,1-dioxide and 5.7 g of 4-methyl-7-amino-coumarin are dissolved in 280 ml of xylene and the solution is heated for 2½ hours in a bath of 170° C. to distill off the methanol formed during the reaction. The reaction mixture is refluxed for a further 5 hours, cooled, and the precipitate is collected by filtration. The precipitate is digested with 100 ml of 2N-hydrochloric acid at elevated temperature, treated with 100 ml of chloroform and extracted. The residue is collected by suction, washed successively with water, ethanol, methylene chloride and diethyl ether, washed, and dried, affording 2-methyl-3,4-dihydro-4-oxo-N-(2-oxo-4-methyl-2H-1-benzopyran-7-yl)-2H-1,2-benzothiazine-3-carboxamide 1,1-dioxide with a melting point above 285° C.

EXAMPLE 4

A solution of 6 g of 2-methyl-N-(4-oxo-4H-1-benzopyran-3-yl)-4-(1-pyrrolidinyl)-2H-1,2-benzothiazine-3-carboxamide 1,1-dioxide in 150 ml of glacial acetic acid is heated on a steam bath. Then 150 ml of 2 N hydrochloric acid are added and after heating for 45 minutes, the reaction mixture is diluted with ice-water to a volume of 1.5 liters and filtered, affording in almost quantitative yield a product with a melting point of 290° C. (with decomp.). According to the mixed melting point and IR spectrum this product is identical with the substance obtained by reaction of 2-methyl-4-oxo-3,4-dihydro-2H-1,2-benzthiazine-3-carboxylic acid methyl ester 1,1-dioxide with 3-amino-4-oxo-4H-1-benzopyrane as described in Example 1, i.e. 2-methyl-3,4-dihydro-4-oxo-N-(4-oxo-4H-1-benzopyran-3-yl)-2H-1,2-benzothiazine-3-carboxamide 1,1-dioxide with a melting point of 290° C. (with decomp.).

The starting material can be prepared for example as follows:

A solution of 2.5 g (0.025 mole) of phosgene in toluene is diluted with 50 ml of dry tetrahydrofurane and then cooled to a temperature of −40° C. A solution of 6.6 g (0.025 mole) of 2-methyl-4-(1-pyrrolidinyl)-2H-1,2-benzothiazine 1,1-dioxide and 2.5 g (0.025 mole) of triethylamine in 200 ml of tetrahydrofurane is then added slowly, with stirring, at a temperature of −40° to +55° C. in the course of 30 minutes. The reaction mixture is stirred for 12 hours at room temperature, then cooled to 10° C., and subsequently a suspension of 6.25 g (0.05 mole) of 3-amino-4-oxo-4H-1-benzopyrane in 100 ml of tetrahydrofurane is added slowly. The temperature of the reaction mixture is allowed to rise to room temperature. The reaction mixture is then stirred for 72 hours and poured into ice-water. The precipitate is collected by suction and crystallised from tetrahydrofurane, affording pure crystalline 2-methyl-N-(4-oxo-4H-1-benzopyran-3-yl)-4-(1-pyrrolidinyl)-2H-1,2-benzothiazine-3-carboxamide 1,1-dioxide. 2-Methyl-3,4-dihydro-4-oxo-N-(6-chloro-7-methyl-4-oxo-4H-1-benzopyran-3-yl)-2H-1,2-benzothiazine-3-carboxamide 1,1-dioxide can be obtained in analogeous manner starting from 2-methyl-N-(6-chloro-7-methyl-4-oxo.4H-1-benzopyran-3-yl)-4-(1-pyrrolidinyl)-1,2-benzothiazine-3-carboxamide 1,1-dioxide.

EXAMPLE 5

About 1 g of sodium methylate is added, under nitrogen, to a solution of 4 g of crude 2-methoxycarbonyl-N-methyl-N-[N'-(4-oxo-4H-1-benzopyran-3-yl)-carbamoyl-methyl]-benzenesulfamide in 50 ml of absolute dimethyl formamide. The reaction mixture is heated cautiously to 80° C. and then evaporated to dryness in vacuo. Water is added to the residue and after neutralisation with 2 N-hydrochloric acid, the crude 2-methyl-3,4-dihydro-4-oxo-N-(4-oxo-4H-1-benzopyran-3-yl)-2H-1,2-benzothiazine-3-carboxamide 1,1-dioxide is separated and purified as in Example 1 and also by chromatography on silica gel. It melts at 280° C.

The starting material can be prepared for example as follows:

10 ml of chloroform are added to 8 g of 3-aminochromone in 200 ml of toluene and the mixture is warmed to 40° C. After cooling to 20° C., 10 ml of N,N-diisopropylethylamine are added with stirring, followed by the addition of 4.8 ml of bromoacetyl chloride in 20 ml of toluene at 10° C. in the course of 5 minutes. When the addition is complete, the reaction mixture is stirred for 1 hour at room temperature. The crystalline precipitate which has formed is collected by suction, washed with water and recrystallised from ethanol/petroleum ether, yielding 11.8 g of 2-bromo-N-(4-oxo-1-benzopyran-3-yl)-acetamide with a melting point of 198° C.

A solution of 7.5 g of 2-bromo-N-(4-oxo-1-benzopyran-3-yl)-acetamide and 5.5 g of saccharin sodium in 100 ml of absolute dimethyl formamide is heated for 5 hours to 100° C., then cooled to room temperature. The crystalline precipitate is collected by filtration and washed with ethanol, yielding 8.6 g of 2-(1,1,3-trioxo-2,3-dihydro-benzothiazol-2-yl)-N-(4-oxo-1-benzopyran-3-yl)-acetamide with a melting point of 280°–281° C.

To a solution of 3.8 g of the above product in 100 ml of dimethyl formamide is added 0.7 g of sodium methylate. The mixture is heated briefly to 80° C., then cooled to 30° C. After addition of 2 g of methyl iodide the reaction mixture is stirred for 2 hours at 30° C., then heated slowly to about 70° C. and concentrated in vacuo to half its volume. The 2-methoxycarbonyl-N-methyl-N-[N'-(4-oxo-4H-1-benzopyran-3-yl)-carbamoyl-methyl]-benzenesulfamide contained in the reaction mixture is further processed direct.

EXAMPLE 6

With stirring, 10 ml of the mixed anhydride of formic and acetic acid are added at room temperature to 4 g of 2-methyl-N-[(2-hydroxy)-benzoylmethyl]-3,4-dihydro-2H-1,2-benzothiazine-3-carboxamide 1,1-dioxide and 1.4 g of sodium formiate. The reaction mixture is stirred for 1 hour and then heated for 3 hours to about 100° C. After cooling to room temperature, 200 ml of water are added. The crude 2-methyl-4-oxo-N-(4-oxo-4H-1-benzopyran-3-yl)-3,4-dihydro-2H-1,2-benzothiazine 1,1-dioxide is separated and purified as described in Example 1 and by subsequent chromatography on silica gel. The product melts at 280° C. The starting material can be obtained for example starting from α-amino-2-hydroxy-acetophenone and 2-methyl-4-oxo-3,4-dihydro-1,2-benzothiazine-3-carboxylic acid methyl ester 1,1-dioxide by the procedure described in Example 1. Melting point: 256°–258° C., recrystallisation from dimethyl formamide/ethanol (1:10).

EXAMPLE 7

5 g of 2-methyl-4-oxo-(N-4-oxo-4H-1,4-benzopyran-3-yl)-3,4-dihydro-2H-1,2-benzothiazine-3-carboxamide 1,1-dioxide are dissolved at 50° C. in a mixture of 125 ml of 0.1 N sodium hydroxide solution and 100 ml of methanol. The solution is cooled to 5° C. and the yellow crystals of the sodium monohydrate of 2-methyl-4-oxo-N-(4-oxo-4H-1,4-benzopyran-3-yl)-3,4-dihydro-2H-1,2-benzothiazine-3-carboxamide 1,1-dioxide are collected. Melting point: 240°–245° C. (with decomp.).

EXAMPLE 8

5 g of the sodium monohydrate of 2-methyl-4-oxo-N-(4-oxo-4H-1,4-benzopyran-3-yl)-3,4-dihydro-2H-1,2-benzothiazine-3-carboxamide 1,1-dioxide are dissolved in 900 ml of methanol and 400 ml of water. A solution of 1.65 g of zinc sulfate dihydrate in 50 ml of water is added to the above solution, yielding the zinc salt of 2-methyl-4-oxo-N-(4-oxo-4H-1,4-benzopyran-3-yl)-3,4-dihydro-2H-1,2-benzothiazine-3-carboxamide 1,1-dioxide with a melting point of 280° C. (with decomp.).

EXAMPLE 9

5 g of the sodium monohydrate of 2-methyl-4-oxo-N-(4-oxo-4H-1,4-benzopyran-3-yl)-3,4-dihydro-2H-1,2-benzothiazine-3-carboxamide 1,1-dioxide are dissolved in 1000 ml of methanol and 200 ml of water. To this solution is added a solution of 1.2 g of copper acetate, yielding the copper salt of 2-methyl-4-oxo-N-(4-oxo-4H-1,4-benzopyran-3-yl)-3,4-dihydro-2H-1,2-benzothiazine-3-carboxamide 1,1-dioxide with a melting point above 300° C.

EXAMPLE 10

Nitrogen is blown for 5 minutes into a mixture of 12.7 g of 4-oxo-3,4-dihydro-2H-1,2-benzothiazine-3-carboxylic acid methyl ester 1,1-dioxide and 9.7 g of 3-amino-4-oxo-4H-1-benzopyrane in 500 ml of xylene. The reaction mixture is slowly heated to the boil and distilled for 15 hours while replenishing the solvent from time to time. After cooling to 50° C., the precipitate is collected by suction, washed with ethanol and dried, yielding 4-oxo-N-(4-oxo-N-4H-1,4-benzopyran-3-yl)-3,4-dihydro-2H-1,2-benzothiazine-3-carboxamide 1,1-dioxide with a melting point of 288° to 290° C.

Reaction of this compound with a reactive ethanol ester, for example ethyl iodide, yields 2-ethyl-4-oxo-N-(4-oxo-4H-1,4-benzopyran-3-yl)-3,4-dihydro-2H-1,2-benzothiazine-carboxamide 1,1-dioxide, and reaction with a reactive allyl alcohol ester, for example allyl bromide, yields 2-allyl-4-oxo-N-(4-oxo-4H-1,4-benzopyran-3-yl)-3,4-dihydro-2H-1,2-benzothiazine-carboxamide 1,1-dioxide. Melting point: 200° C.

EXAMPLE 11

Tablets containing 25 mg of 2-methyl-3,4-dihydro-4-oxo-N-(4H-1-benzopyran-3-yl)-2-H-1,2-benzothiazine-3-carboxamide 1,1-dioxide can be manufactured for example as follows: Composition (for 10,000 tablets):

| | |
|---|---|
| 2-methyl-3,4-dihydro-4-oxo-N-(4H-1-benzopyran-3-yl)-2H-1,2-benzothiazine-3-carboxamide 1,1-dioxide (active substance) | 250 g |
| lactose | 460 g |
| corn starch | 650 g |
| polyvinyl pyrrolidone | 20 g |
| magnesium stearate | 10 g |
| colloidal silica | 10 g |
| water | as required |

The active substance, lactose and 450 g of the corn starch are mixed and moistened with an aqueous solution of polyvinyl pyrrolidone. The mixture is granulated and dried and the granulate is mixed with the magnesium stearate, the colloidal silica and the remainder of the corn starch. The mixture is forced through a sieve, mixed and pressed to tablets of 140 mg (diameter: 7 mm).

EXAMPLE 12

Tablets containing 25 mg of each of the following compounds can also be manufactured as described in Example 11:

2-methyl-3,4-dihydro-4-oxo-N-(4,6,7,8-tetrahydro-4-oxo-cyclopenta[g]-1-benzopyran-3-yl)-2H-1,2-benzothiazine-3-carboxamide 1,1-dioxide, 2-methyl-3,4-dihydro-4-oxo-N-(4-oxo-6-methyl-4H-1-benzopyran-3-yl)-2H-1,2-benzothiazine-3-carboxamide 1,1-dioxide, 2-methyl-3,4-dihydro-4-oxo-N-(4-oxo-8-methyl-4H-1-benzopyran-3-yl)-2H-1,2-benzothiazine-3-carboxamide 1,1-dioxide, 2-methyl-3,4-dihydro-4-oxo-N-(2-oxo-4-hydroxy-6-methyl-2H-1-benzopyran-3-yl)-2H-1,2-benzothiazine-3-carboxamide 1,1-dioxide, 2-methyl-3,4-dihydro-4-oxo-N-(4-oxo-6,7-dimethyl-4H-1-benzopyran-3-yl)-2H-1,2-benzothiazine-3-carboxamide 1-dioxide, 2-methyl-3,4-dihydro-4-oxo-N-(4-oxo-6-methoxy-4H-1-benzopyran-3-yl)-2H-1,2-benzothiazine-3-carboxamide 1,1-dioxide, 2-methyl-3,4-dihydro-4-oxo-N-(4-oxo-5,7-dimethyl-4H-1-benzopyran-3-yl)-2H-1,2-benzothiazine-3-carboxamide 1,1-dioxide.

2-methyl-3,4-dihydro-4-oxo-N-(2-oxo-4-hydroxy-6-chlor-2H-1-benzopyran-3-yl)-2H-1,2-benzothiazine-3-carboxamide 1,1-dioxide, 2-methyl-3,4-dihydro-3-oxo-N-(2-oxo-4-hydroxy-6,8-dichlor-2H-1-benzopyran-3-yl)-2H-1,2-benzothiazine-3-carboxamide 1,1-dioxide, 2-methyl-3,4-dihydro-4-oxo-N-(2-oxo-4-hydroxy-4,6,7,8-tetrahydro-cyclopenta[g]-2H-1-benzopyran-3-yl)-2H-1,2-benzothiazine-3-carboxamide 1,1-dioxide, 2-methyl-3,4-dihydro-4-oxo-N-(2-oxo-4-hydroxy-8-methyl-2H-1-benzopyran-3-yl)-2H-1,2-benzothiazine-3-carboxamide 1,1-dioxide and 2-methyl-3,4-dihydro-4-oxo-N-(2-oxo-4-methyl-2H-1-benzopyran-7yl)-2H-1,2-benzothiazine-3-carboxamide 1,1-dioxide.

EXAMPLE 13

Tablets containing 25 mg of each of the following compounds can also be manufactured as described in Example 11:

2-methy-N-(6-chloro-8-methyl-4-oxo-4H-1-benzopyran-3-yl)-4-oxo-3,4-dihydro-4H-1-benzo-pyran-3-yl)-3-carboxamide 1,1-dioxide, 2-methyl-3,4-dihydro-4-oxo-N-(6-chloro-7-methyl-4-oxo-4H-1-benzopyran-3-yl)-2H-1,2-benzothiazine-3-carboxamide 1,1-dioxide, Sodium monohydrate of 2-methyl-4-oxo-N-(4-oxo-4H-1,4-benzopyran-3-yl)-3,4-dihydro-2H-1,2-benzothiazine-3-carboxamide 1,1-dioxide, 2-methyl-3,4-dihydro-4-oxo-N-(4,6,7,8-tetrahydro-4-oxo-cyclopenta[g]-1-benzopyran-3-yl)-2H-1,2-benzothiazine-3-carboxamide 1,1-dioxide, sodium hydrate, 2-methyl-3,4-dihydro-4-oxo-N-(4-oxo-6,7-dimethyl-4H-1-benzopyran-3-yl)-2H-1,2-benzothiazine-3-carboxamide 1-dioxide, sodium hydrate, 2-methyl-3,4-dihydro-4-oxo-N-(4-oxo-6-methoxy-4H-1-benzopyran-3-yl)-2H-1,2-benzothiazine-3-carboxamide -1,1-dioxide, sodium hydrate, 2-methyl-3,4-dihydro-4-oxo-N-(4-oxo-5,7-dimethyl-4H-1-benzopyran-3-yl)-2H-1,2-benzothiazine-3-carboxamide 1,1-dioxide, sodium hydrate, 2-methyl-3,4-dihydro-4-oxo-N-(4-oxo-8-methyl-4H-1-benzopyran-3-yl)-2H-1,2-benzothiazine-3-carboxamide 1,1-dioxide, 2-methyl-3,4-dihydro-4-oxo-N-(4-oxo-8-methyl-4H-1-benzopyran-3-yl)-2H-1,2-benzothiazine-3-carboxamide 1,1-dioxide, sodium hydrate, 2-methyl-3,4-dihydro-4-oxo-N-4-oxo-6-methyl-4H-1-benzopyran-3-yl)-2H-1,2-benzothiazine-3-carboxamide 1,1-dioxide, sodium hydrate, 4-oxo-N-(4oxo-4H-1,4-benzopyran-3-yl)-3,4-dihydro-2H-1,2-benzothiazine-3-carboxamide 1,1-dioxide, 2-ethyl-4-oxo-N-(4-oxo-4H-1,4-benzopyran-3-yl)-3,4-dihydro-2H-1,2-benzothiazine-3-carboxamide 1,1-dioxide and 2-allyl-4-oxo-N-(4-oxo-4H-1,3-benzopyran-3-yl)-3,4-dihydro-2H-1,2-benzothiazine-3-carboxamide 1,1-dioxide.

EXAMPLE 14

In an analogous manner as described in Example 7, the following compounds can also be prepared:

Sodium monohydrate of 2-methyl-N-(6-chloro-7-methyl-4-oxo-4H-1-benzo-pyran-3-yl)-4-oxo-3,4-dihydro-4H-1-benzopyran-3-yl)-3-carboxamide 1,1-dioxide, m.p. 239°–241°, sodium monohydrate of 2-methyl-3,4-dihydro-4-oxo-N-(4,6,7,8-tetrahydro-4-oxo-cyclopenta[g]-1-benzopyran-3-yl)-2H-1,2-benzothiazine-3-carboxamide 1,1-dioxide, m.p. 240°–241°, sodium monohydrate of 2-methyl-3,4-dihydro-4-oxo-N-(4-oxo-6,7-dimethyl-4H-1-benzopyran-3-yl)-2H-1,2-benzothiazine-3-carboxamide 1-dioxide, m.p. 260°–261°, sodium monohydrate of 2-methyl-3,4-dihydro-4-oxo-N-(4-oxo-6-methoxy-4H-1-benzopyran-3-yl)-2H-1,2-benzothiazine-3-carboxamide 1,1-dioxide, m.p. 235°–239°, sodium monohydrate of 2-methyl-3,4-dihydro-4-oxo-N-(4-oxo-5,7-dimethyl-4H-1-benzopyran-3-yl)-2H-1,2-benzothiazine-3-carboxamide 1,1-dioxide, m.p. 234°–236°, sodium monohydrate of 2-methyl-3,4-dihydro-4-oxo-N-(4-oxo-8-methyl-4H-1-benzopyran-3-yl)-2H-1,2-benzothiazine-3-carboxamide 1,1-dioxide, m.p. 237°–241° and sodium monohydrate of 2-methyl-3,4-dihydro-4-oxo-N-(4-oxo-6-methyl-4H-1-benzopyran-3-yl)-2H-1,2-benzothiazine-3-carboxamide 1,1-dioxide, m.p. 235°–239°.

We claim:

1. A substituted 3,4-dihydro-2H-1,2-benzothiazine 1,1-dioxide of the formula

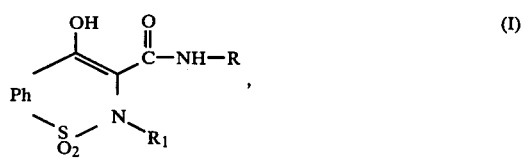

wherein Ph represents 1,2-phenylene or 1,2-phenylene substituted by lower alkyl, lower alkoxy, lower alkanoyl, halogen, trifluoromethyl or nitro, R represents benzopyrone or benzopyrone substituted by lower alkyl, lower alkoxy, halogen, hydroxy, lower alkanoyloxy, optionally lower-alkylated or lower-alkanoylated amino, trifluoromethyl or, at two adjacent carbon atoms, by lower alkylene or lower alkylenedioxy, and $R_1$ represents hydrogen, lower alkyl, hydroxy-lower alkyl, lower alkoxy-lower alkyl, lower alkenyl, phenyl-lower alkyl or phenyl-lower alkyl substituted by lower alkyl, lower alkoxy, halogen, trifluoromethyl or nitro or a pharmaceutically acceptable salt thereof.

2. A compound as claimed in claim 1, wherein Ph represents a 1,2-phenylene radical which is unsubstituted or substituted by lower alkyl of not more than 4 carbon atoms, lower alkoxy of not more than 4 carbon atoms, halogen with an atomic number up to 35, nitro or trifluoromethyl, R represents a 2-oxo-2H-1-benzopyranyl radical which is bonded in the 3-, 4-, 6- or 7-position or a 4-oxo-4H-1-benzopyranyl radical which is bonded in the 3-, 6- of 7-position, and which is unsubstituted or substituted by lower alkyl of not more than 4 carbon atoms, lower alkoxy of not more than 4 carbon atoms, halogen with an atomic number up to 35, lower alkanoyloxy of not more than 4 carbon atoms, hydroxyl, amino, N-mono- or N,N-di-lower alkylamino containing not more than 4 carbon atoms in the alkyl moiety, lower alkanoylamino of not more than 4 carbon atoms, or at two adjacent carbon atoms by lower alkylene of not more than 4 carbon atoms, or lower alkylenedioxy of not more than 4 carbon atoms, and $R_1$ represents hydrogen or lower alkyl of not more than 4 carbon atoms, or a pharmaceutically acceptable salt thereof with a base.

3. A compound as claimed in claim 1 of the formulae Ib and Ic

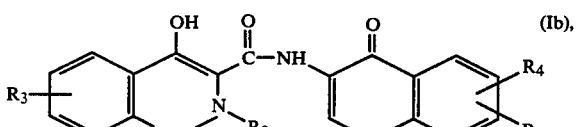

and

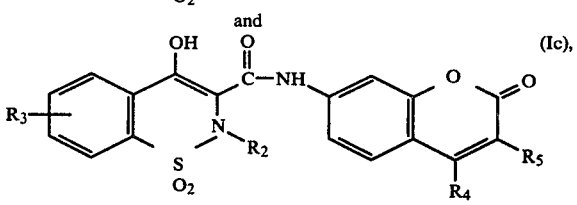

wherein $R_2$ represents hydrogen or lower alkyl of not more than 4 carbon atoms, $R_3$ represents hydrogen, lower alkyl of not more than 4 carbon atoms, lower alkoxy of not more than 4 carbon atoms, halogen with an atomic number up to 35, trifluoromethyl or nitro, and $R_4$ and $R_5$, each independently of the other, represent hydrogen, lower alkyl of not more than 4 carbon atoms, or lower alkoxy of not more than 4 carbon atoms, or together they represent a 3- or 4-membered lower alkylene or lower alkylenedioxy radical of not more than 4 carbon atoms which is bonded to adjacent carbon atoms, or in formula Ic, $R_4$ represents hydroxyl and $R_5$ represents hydrogen or lower alkyl of not more than 4 carbon atoms, or a pharmaceutically acceptable salt thereof with a base.

4. A compound as claimed in claim 1 of the formulae Ib and Ic

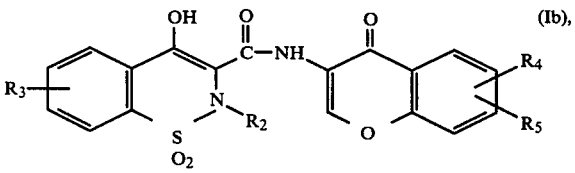

and

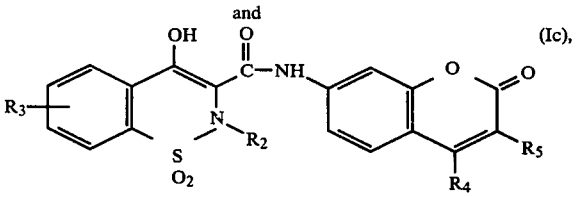

wherein $R_2$ represents lower alkyl of not more than 4 carbon atoms, $R_3$ represents hydrogen, and each of $R_4$ and $R_5$ independently represents hydrogen, lower alkyl or lower alkoxy of not more than 4 carbon atoms, or a pharmaceutically acceptable salt thereof with a base.

5. A compound as claimed in claim 1 being 2-Methyl-3,4-dihydro-4-oxo-N-(4-oxo-4H-1-benzopyran-3-yl)-2H-1,2-benzothiazine-3-carboxamide 1,1-dioxide, or a salt thereof with a base.

6. A compound as claimed in claim 1 being 2-Methyl-3,4-dihydro-4-oxo-N-(2-oxo-4-methyl-2H-1-benzopyran-7-yl)-2H-1,2-benzothiazine-3-carboxamide 1,1-dioxide or a salt thereof with a base.

7. A compound as claimed in claim 1 being 2-Methyl-3,4-dihydro-4-oxo-N-(4-oxo-4,6,7,8-tetrahydrocyclopenta[g]-1-benzopyran-3-yl)-2H-1,2-benzothiazine-3-carboxamide 1,1-dioxide or a salt thereof with a base.

8. A compound as claimed in claim 1 being 2-Methyl-3,4-dihydro-4-oxo-N-(2-oxo-4-hydroxy-6-methyl-2H-1-benzopyran-3-yl)-2H-1,2-benzothiazine-3-carboxamide 1,1-dioxide, 2-Methyl-3,4-dihydro-4-oxo-N-(4-oxo-6,7-dimethyl-4H-1-benzopyran-3-yl)2H-1,2-benzothiazine-3-carboxamide 1,1-dioxide, 2-Methyl-3,4-dihydro-4-oxo-N-(4-oxo-6-methoxy-4H-1-benzopyran-3-yl)-2H-1,2-benzothiazine-3-carboxamide 1,1-dioxide, 2-Methyl-3,4-dihydro-4-oxo-N-(4-oxo-5,7-dimethyl-4H-1-benzopyran-3-yl)-2H-1,2-benzothiazine-3-carboxamide 1,1-dioxide, 2-Methyl-3,4-dihydro-4-oxo-N-(4-oxo-8-methyl-4H-1-benzopyran-3-yl)-2H-1,2-benzothiazine-3-carboxamide 1,1-dioxide, 2-Methyl-3,4-dihydro-4-oxo-N-(4-oxo-6-methyl-4H-1-benzopyran-3-yl)-2H-1,2-benzothiazine-3-carboxamide 1,1-dioxide, 2-Methyl-3,4-dihydro-4-oxo-N-(2-oxo-4-hydroxy-6-chlor-2H-1-benzopyran-3-yl)-2H-1,2-benzothiazine-3-carboxamide 1,1-dioxide, 2-Methyl-3,4-dihydro-4-oxo-N-(2-oxo-4-hydroxy-6,8-dichlor-2H-1-benzohydran-3-yl)-2H-1,2-benzothiazine-3-carboxamide 1,1-dioxide, 2-Methyl-3,4-dihydro-4-dihydro-4-oxo-N-(2-oxo-4-hydroxy-4,6,7,8-tetrahydrocyclopenta[g]-1-benzopyran-3-yl)-2H-1,2-benzothiazine-3-carboxamide 1,1-dioxide, 2-Methyl-3,4-dihydro-4-oxo-N-(2-oxo-4-hydroxy-8-methyl-2H-1-benzopyran-3-yl):2H-1,2-benzothiazine-3-carboxamide 1,1-dioxide, 2-Methyl-3,4-dihydro-4-oxo-N-(4-oxo-6-chlor-8-methyl-4H-1-benzopyran-3-yl)-2H-1,2-benzothiazine-3-carboxamide 1,1-dioxide, 3,4-Dihydro-4-oxo-N-(4-oxo-4H-1-benzopyran-3yl)-2H-1,2-benzothiazine-3-carboxamide 1,1-dioxide, 2-Ethyl-3,4-dihydro-4-oxo-N-(4-oxo-4H-1-benzo-pyran-3-yl)-2H-1,2-benzothiazine-3-carboxamide 1,1-dioxide, or 2-Allyl-3,4-dihydro-4-oxo-N-(4-oxo-4H-1-benzopyran-3-yl)-2H-1,2-benzothiazine-3-carboxamide 1,1-dioxide, or a pharmaceutically acceptable salt thereof with a base.

9. A compound as claimed in claim 1 being the sodium salt of 2-Methyl-3,4-dihydro-4-oxo-N-(4-oxo-4H-1-benzopyran-3-yl)-2H-1-benzthiazine-3-carboxamide 1,1-dioxide.

10. A pharmaceutical preparation containing an antiinflammatorically effective amount of a compound as claimed in claim 1 or a pharmaceutically acceptable salt thereof with a base, together with conventional adjuvants or carriers.

* * * * *